US006291188B1

(12) United States Patent
Meade et al.

(10) Patent No.: US 6,291,188 B1
(45) Date of Patent: *Sep. 18, 2001

(54) METALLIC SOLID SUPPORTS MODIFIED WITH NUCLEIC ACIDS

(75) Inventors: Thomas J. Meade, Altadena; Jon F. Kayyem, Pasadena, both of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/639,311

(22) Filed: Aug. 15, 2000

Related U.S. Application Data

(63) Continuation of application No. 08/808,750, filed on Feb. 28, 1997, which is a continuation of application No. 08/475,051, filed on Jun. 7, 1995, now Pat. No. 5,824,473.

(51) Int. Cl.[7] ....................................................... C12Q 1/68
(52) U.S. Cl. .................................. 435/6; 435/7.1; 427/58
(58) Field of Search ........................ 435/6, 7.1; 536/24.3; 427/58

(56) References Cited

U.S. PATENT DOCUMENTS

| 4,707,352 | 11/1987 | Stavrianopoulos . |
| 4,707,440 | 11/1987 | Stavrianopoulos ........................ 435/6 |
| 4,711,955 | 12/1987 | Ward et al. . |
| 4,755,458 | 7/1988 | Rabbani et al. . |
| 4,840,893 | 6/1989 | Hill et al. .................................. 435/6 |
| 4,849,513 | 7/1989 | Smith et al. ............................. 536/27 |
| 4,868,103 | 9/1989 | Stavrianopoulos et al. . |
| 4,894,325 | 1/1990 | Englehardt et al. . |
| 4,943,523 | 7/1990 | Stavrianopoulos . |
| 4,952,685 | 8/1990 | Stavrianopoulos . |
| 4,994,373 | 2/1991 | Stavrianopoulos . |
| 5,002,885 | 3/1991 | Stavrianopoulos . |
| 5,013,831 | 5/1991 | Stavrianopoulos . |
| 5,082,830 | 1/1992 | Brakel et al. . |

(List continued on next page.)

FOREIGN PATENT DOCUMENTS

| 2 090904 | 9/1993 | (CA) . |
| 0 63879 | 11/1982 | (EP) . |
| 0 234938 | 2/1987 | (EP) . |
| 0 229943 | 7/1987 | (EP) . |
| 0 599337 | 1/1994 | (EP) . |
| 0 589 867 | 4/1996 | (EP) . |
| 0515615 | 9/1996 | (EP) . |
| 238166 | 10/1988 | (JP) . |
| 6-41183 | 2/1994 | (JP) . |
| 90/05303 | 5/1990 | (WO) . |
| 90/05732 | 5/1990 | (WO) . |
| 92/10757 | 6/1992 | (WO) . |
| 93/10267 | 5/1993 | (WO) . |
| 93/22678 | 11/1993 | (WO) . |
| 93/23425 | 11/1993 | (WO) . |
| 94/22889 | 10/1994 | (WO) . |
| 95/15971 | 6/1995 | (WO) . |
| 96/40712 | 12/1996 | (WO) . |
| 97/01646 | 1/1997 | (WO) . |
| 97/27329 | 7/1997 | (WO) . |
| 97/44651 | 11/1997 | (WO) . |
| 98/20162 | 5/1998 | (WO) . |
| 98/27229 | 6/1998 | (WO) . |
| 98/28444 | 7/1998 | (WO) . |
| 98/35232 | 8/1998 | (WO) . |
| 99/14596 | 3/1999 | (WO) . |
| 99/67425 | 12/1999 | (WO) . |

OTHER PUBLICATIONS

Alleman, K.S., et al., "Electrochemical Rectification at a Monolayer–Modified Electrode," *J. Phys. Chem.*, 100:17050–17058 (1996).

Arkin et al. "Evidence for Photoelectron Transfer Through DNA Intercalation," *J. Inorganic Biochem. Abstracts*, 6th International Conference on Bioinorganic Chemistry, 51(1) & (2):526 (1993).

Barisci et al., "Conducting Polymer Sensors," *Trip*, 4(9):307–311 (1996).

Baum, R. M., "Views on Biological, Long–Range Electron Transfer Stir Debate," *C& EN*, pp. 20–23 (1993).

Bechtold, R., et al., "Ruthenium–Modified Horse Heart Cytochrome c: Effect of pH and Ligation on the Rate on Intramolecular Electron Transfer between Ruthenium(II) and Heme(III)," *J. Phys. Chem.*, 90(16):3800–3804 (1986).

Bidan, "Electroconducting conjugated polymers: new sensitive matrices to build up chemical or electrochemical sensors. A Review.," *Sensors and Actuators*, B6: 45–56 (1992).

Biotechnology and Genetics: Genetic Screening Integrated Circuit, *The Economist* (Feb. 25–Mar. 3, 1995).

Boguslavsky, L. et al., "Applications of redox polymers in biosensors," *Solid State Ionics*, 60:189–197 (1993).

(List continued on next page.)

*Primary Examiner*—Scott W. Houtteman
(74) *Attorney, Agent, or Firm*—Richard F. Trecartin; Robin M. Silva; Flehr Hohbach Test Albritton & Herbert LLP

(57) ABSTRACT

The present invention provides for the selective covalent modification of nucleic acids with redox active moieties such as transition metal complexes. Electron donor and electron acceptor moieties are covalently bound to the ribose-phosphate backbone of a nucleic acid at predetermined positions. The resulting complexes represent a series of new derivatives that are bimolecular templates capable of transferring electrons over very large distances at extremely fast rates. These complexes possess unique structural features which enable the use of an entirely new class of bioconductors and photoactive probes.

35 Claims, No Drawings

U.S. PATENT DOCUMENTS

| | | |
|---|---|---|
| 5,175,269 | 12/1992 | Stavrianopoulos . |
| 5,241,060 | 8/1993 | Englehardt et al. . |
| 5,242,828 | 9/1993 | Bergstrom et al. . |
| 5,278,043 | 1/1994 | Bannwarth et al. ............... 536/23.1 |
| 5,312,527 | 5/1994 | Mikkelsen et al. ............. 204/153.12 |
| 5,328,824 | 7/1994 | Ward et al. . |
| 5,403,451 | 4/1995 | Riviello et al. .................... 204/153.1 |
| 5,436,161 | 7/1995 | Bergstrom et al. . |
| 5,449,767 | 9/1995 | Ward et al. . |
| 5,472,881 | 12/1995 | Beebe et al. ........................... 436/94 |
| 5,476,928 | 12/1995 | Ward et al. . |
| 5,552,270 | 9/1996 | Khrapko et al. . |
| 5,565,552 | 10/1996 | Magda et al. .......................... 534/11 |
| 5,571,568 | * 11/1996 | Ribi et al. . |
| 5,573,906 | 11/1996 | Bannwarth et al. ..................... 435/6 |
| 5,591,578 | 1/1997 | Meade et al. ............................ 435/6 |
| 5,595,908 | 1/1997 | Fawcett et al. ................... 435/287.2 |
| 5,601,982 | 2/1997 | Sargent et al. ........................... 435/6 |
| 5,620,850 | 4/1997 | Bamdad et al. ..................... 530/300 |
| 5,705,348 | 1/1998 | Meade et al. ............................ 435/6 |
| 5,741,700 | 4/1998 | Ershov et al. . |
| 5,756,050 | 5/1998 | Ershov et al. . |
| 5,770,369 | 6/1998 | Meade et al. ............................ 435/6 |
| 5,770,721 | 6/1998 | Ershov et al. . |
| 5,776,672 | 7/1998 | Hashimoto et al. . |
| 5,780,234 | 7/1998 | Meade et al. ............................ 435/6 |
| 5,824,473 | 10/1998 | Meade et al. ............................ 435/6 |
| 5,851,772 | 12/1998 | Mirzabekov et al. . |
| 5,952,172 | 9/1999 | Meade et al. . |

OTHER PUBLICATIONS

Bowler, B. E., et al., "Long–Range Electron Transfer in Donor (Spacer) Acceptor Molecules and Proteins," *Progress in Inorganic Chemistry: Bioinorganic Chemistry,* 38:259–322 (1990).

Brun, A. M., et al., "Photochemistry of Intercalated Quaternary Diazaaromatic Salts," *J. Am. Chem. Soc.,* 113:8153–8159 (1991).

Bumm, et al., "Are Single Molecular Wires Conducting?," *Science* 271:1705–1707 (1996).

Cantor, C.R. et al., "Report on the Sequencing by Hybridization Workshop," *Genomics,* 13:1378–1383 (1992).

Chang, I–Jy, et al., "High–Driving–Force Electron Transfer in Metalloproteins: Intramolecular Oxidation of Ferrocytochrome c by Ru(2,2'–bpy)$_2$(im)(His–33)$^{3+}$," *J. Am. Chem. Soc.,* 113:7056–7057 (1991).

Chidsey, C.E.D., et al.,"Free Energy and Temperature Dependence of Electron Transfer at the Metal Electrolyte Interface," *Science,* 251:919–923 (1991).

Chidsey, et al., "Coadsorption of Ferrocene–Terminated and Unsubstituted Alkanethiols on Gold Electroactive Self–Assembled Monolayers," *J. Am. Chem. Soc.,* 112:4301–4306 (1990).

Chrisey, et al., "Covalent attachment of synthetic DNA to self–assembled monolayer films," *Nucleic Acids Research,* 24(15):3031–3039 (1996).

Clery, "DNA Goes Electric," *Science,* 267:1270 (1995).

*Commerce Business Daily* Issue of Sep. 26, 1996 PSA#1688.

Davis, L. M., et al., "Electron Donor Properties of the Antitumour Drug Amsacrine as Studied by Fluorescence Quenching of DNA–Bound Ethidium," *Chem.–Biol. Interactions,* 62:45–58 (1987).

Davis, L. M., et al., "Elements of biosensor construction," *Enzyme Microb. Technol.* 17:1030–1035 (1995).

Degani et al., "Direct Electrical Communication between Chemically Modified Enzymes and Metal Electrodes. 2. Methods for Bonding Electron–Transfer Relays to Glucose Oxidase and D–Amino–Acid Oxidase," *J. Am. Chem. Soc.* 110:2615–2620 (1988).

Degani, Y., et al., "Electrical Communication between Redox Centers of Glucose Oxidase and Electrodes via Electrostatically and Covalenty Bound Redox Polymers," *J. Am. Chem. Soc.,* 111:2357–22358 (1989).

Degani, Y., et al., "Direct Electrical Communication between Chemically Modified Enzymes and Metal Electrodes. 1. Electon Transfer from Glucose Oxidase to Metal Electrodes via Electron Relays, Bound Covalently to the Enzyme," *J. Phys. Chem.,* 91(6):1285–1288 (1987).

Deinhammer, R.S., et al., "Electronchemical Oxidation of Amine–containing compounds: A Route to the Surface Modification of glassy carbon electrodes," *Langumuir,* 10:1306–1313 (1994).

Dreyer, G. B., et al., "Sequence–specific cleavage of single–stranded DNA: Oligodeoxynucleotide–EDTA•Fe(II)," *Proc. Natl. Acad. Sci. USA,* 82:968–972 (1985).

Durham, B., et al., "Photoinduced Electron–Transfer Kinetics of Singly Labeled Ruthenium Bis(bipyridin) Dicarboxbipyridine Cytochrome c Derivates," *Biochemistry,* 28:8659–8665 (1989).

Durham, B., et al., "Electron–Transfer Kinetics of Singly Labeled Ruthenium(II) Polypyridine Cytocheome c Derivatives," *Advance in Chemistry Series,* 226:181–193 (1990).

Elias, H., et al., "Electron–Transfer Kinetics of Zn–Substituted Cytochrome c and Its Ru(NH$_3$)$_5$(Histidine–33) Derivative," *J. Am. Chem. Soc.,* 110:429–434 (1988).

Farver, O., et al.,"Long–range intramolecular electron transfer in azurins," *Proc. Natl. Acad. Sci. USA,* 86:6968–6972 (1989).

Fox, L. S., et al., "Gaussian Free–Energy Dependence of Electron–Transfer Rates in Iridium Complexes," *Science,* 247:1069–1071 (1990).

Fox, M. A., et al., "Light–Harvesting Polymer Systems," *C&EN,* pp. 38–48 (Mar. 15, 1993).

Francois, J–C., et al., "Periodic Cleavage of Poly(dA) by Oligothymidylates Covalently Linked to the 1,10–Phenanthroline–Copper Complex," *Biochemistry,* 27:2272–2276 (1988).

Friedman, A. E., et al., "Molecular 'Light Switch' for DNA: Ru(bpy)$_2$(dppz)$^{2+}$," *J. Am. Chem. Soc.,* 112:4960–4962 (1990).

Fromherz, P., et al., "Photoinduced Electron Transfer in DNA Matrix from Intercalated Ethidium to Condensed Methylviologen," *J. Am. Chem. Soc.,* 108:5361–5362 (1986).

Gardner, et al., "Application of conducting polymer technology in microsystems," *Sensors and Actuators,* A51:57–66 (1995).

Gregg, B. A., et al., "Cross–linked redox gels containing glucose oxidase for amperometric biosensor applications," *Anal. Chem.,* 62:258–263 (1990).

Gregg, B. A., et al., "Redox Polymer Films Containing Enzymes. 1. A Redox–Conducting Epoxy Cement: Synthesis, Characterization, and Electrocatalytic Oxidation of Hydroquinone," *J. Phys. Chem.,* 95:5970–5975 (1991).

Hashimoto, et al., "Sequence–Specific Gene Detection with a Gold Electrode Modified with DNA Probes and an Electrochemically Active Dye," *Anal. Chem.* 66:3830–3833 (1994).

Hegner, et al., "Immobilizing DNA on gold via thiol modification for atomic force microscopy imaging in buffer solutions," *FEBS* 336(3):452–456 (1993).

Heller, A., et al., "Amperometric biosensors based on three–dimensional hydrogel–forming epoxy networks," *Sensors and Actuators,* 13–14:180–183 (1993).

Heller, A., "Electrical Wiring of Redox Enzymes," *Acc. Chem. Res.,* 23:128–134 (1990).

Heller et al., "Fluorescent Energy Transfer Oligonucleotide Probes," *Fed. Proc.* 46(6):1968 (1987) Abstract No. 248.

Ho "DNA–Mediated Electron Transfer and Application of 'Biochip'Development," *Abstract. Office of Naval Research* (Report Date: Jul. 25, 1991) 1–4, RR04106.

Hobbs et al., "Polynucleotides Containing 2'–Amino–2'deoxyribose and 2'–Azido–2'–deoxyriose," *Biochemistry,* 12(25):5138–5145 (1973).

Hsung, et al., "Synthesis and Characterization of Unsymmetric Ferrocene–Terminated Phenylethynyl Oligomers," *Organometallics,* 14:4808–4815 (1995).

Hsung, et al., "Thiophenol Protecting Groups for the Palladium–Catalyzed Heck Reaction: Efficient Syntheses of Conjugated Arylthiols," *Tetrahedron Letters.* 36(26):4525–4528 (1995).

Jenkins et al., A sequence–Specific Molecular Light Switch: Tebhering of an Oligonucleotide to a Dipyridophenazine Complex of Ruthenium (II), *J. Am. Chem. Soc.,* 114:8736–8738 (1992).

Katritzky, et al., "Pyridylethylation—A New Protection Method for Active Hydrogen Compounds," *Tetrahedron Letters,*25(12):1223–1226 (1984).

Kelley, S.O. and J.K. Barton, "Electrochemistry of Methylene Blue Bound to a DNA–Modified Electrode," *Bioconjugate Chem.,* 8:31–37 (1997).

Kojima et al., "A DNA Probe of Ruthenium Bipyridine Complex Using Photocatalytic Activity," *Chemistry Letter,* pp. 1889–1982 (1989).

Laviron, E., "A.C. Polarography and Faradaic Impedance of Strongly Adsorbed Electractive Species. Part I: Theoretical and Experimental Study of a Quasi–Reversible Reaction in the Case of a Langmuir Isotherm," *J. Electroanal. Chem.,* 97:135–149 (1979).

Laviron, E., "A.C. Polarography and Faradaic Impedance of Strongly Adsorbed Electractive Species. Part III: Theoretical Complex Plane Analysis for a Surface Redox Reaction," *J. Electroanal. Chem.,* 105:35–42 (1979).

Lee, et al., "Direct Measurement of the Forces Between Complementary Strands of DNA," *Science,* 266:771–773 (1994).

Lenhard, J.R., et al., "Part VII Covalent Bonding of a Reversible– Electrode Reactanbt to Pt Electrodes Using an organosilane Reagent" *J. Electronal. Chem.,* 78:195–201 (1977).

Lipkin "Identifying DNA by the Speed of Electrons," *Science News,* 147(8):117 (1995).

Maskos, et al., "Oligonucleotide hybridisations on glass supports: a novel linker for oligonucletide synthesis and hybridisation properties of oligonucleotides synthesised in situ," *Nucleic Acids Research,* 20(7):1679–1684 (1992).

Mazzocchi, Ph.H. and G. Fritz, "Photolysis of N–(2–Methyl–2–Propenyl)phthalimide in Methanol. Evidence Supporting Radical–Radical Coupling of a Photochemically Generated Radical Ion Pair," *Journal of the American Chemical Society,* 108(18):5361–5362 (1986).

McGee, et al., "2'–Amino–2'–deoxyuridine via an Intramolecular Cyclization of a Trichloroacetimidate," *J. Org. Chem.,* 61:781–785 (1996).

Meade, T. J., "Driving–Force Effects on the Rate of Long–Range Electron Transfer in Ruthenium–Modified Cytochrome c," *J. Am. Chem. Soc.,* 111:4353–4356 (1989).

Meade, T. J., et al., "Electron Transfer through DNA: Site–Specific Modification of Duplex DNA with Ruthenium Donors and Acceptors,"0 *Angew Chem. Int. Ed. Engl.,* 34:352 (1995).

Mestel, "'Electron Highway' Points to Identity of DNA," *New Scientist,* p. 21 (1995).

Millan, et al., "Voltammetric DNA Biosensor for Cystic Fibrosis Based on a Modified Carbon Paste Electrode," *Anal. Chem.,* 66:2943–2948 (1994).

Millan, K.M., et al., "Covalent Immobilization of DNA onto Glassy Carbon Electrodes," *Electroanalysis,* 4(10):929–932 (1992).

Millan, K.M. and Mikkelsen, S.R., "Sequence–Selective Biosensor for DNA Based on Electroactive Hybridization Indicators," *Anal. Chem.,* 65:2317–2323 (1993).

Miller, C., "Absorbed ω–Hydroxy Thiol Monolayers on Gold Electrodes: Evidence for Electron Tunneling to Redox Species in Solution," *J. Phys. Chem.,* 95:877–886 (1991).

Murphy, C. J., et al., "Long–Range Photoinduced Electron Transfer Through a DNA Helix," *Science,* 262:1025–1029 (1993).

Orellana, G., et al., "Photoinduced Electron Transfer Quenching of Excited Ru(II) Polypyridyls Bound to DNA: The Role of the Nucleic Acid Double Helix," *Photochemistry and Photobiology,* 54(4):499–509 (1991).

Palecek, "From Polarography of DNA to Microanalysis with Nucleic Acid–Modified Electrodes," *Electroanalysis.* 8(1):7–14 (1996).

Paterson, "Electric Genes: Current Flow in DNA Could Lead to Faster Genetic Testing," *Scientific American,* 33–34 (May 1995).

Purugganan, M. D., et al., Accelerated Electron Transfer Between Metal Complexes Mediated by DNA, *Science,* 241:1645–1649 (1988).

Rhodes, D. And A. Klug, "Helical Periodicity of DNA Determined by Enzyme Digestion," *Nature,* 286:573–578 (1980).

Risser, S. M., et al., "Electron Transfer in DNA: Predictions of Exponential Growth and Decay of Coupling with Donor–Acceptor Distance," *J. Am. Chem. Soc.,* 115(6):2508–2510 (1993).

Sato, Y., et al., "Unidirectional Electron Transfer at Self-–Assembled Monolayers of 11–Ferrocenyl–1–undecanethiol on Gold," *Bull. Chem. Soc. Jpn.,* 66(4):1032–1037 (1993).

Satyanarayana, S., et al., "Neither Δ– nor Λ–Tris(phenanthroline)ruthenium(II) Binds to DNA by Classical Intercalation," *Biochemistry,* 31(39):9319–9324 (1992).

Schreiber, et al., "Bis(purine) Complexes of trans–$a_2Pt^{11}$: Preparation and X–ray Structures of Bis(9–methyladenine) and Mixed 9–Methyladenine, 9–Methylguanine Complexes and Chemistry Relevant to Metal–Modified Nucleobase Triples and Quartets," *J. Am. Chem. Soc.* 118:4124–4132 (1996).

Schuhmann, W., et al., "Electron Transfer between Glucose Oxidase and Electrodes via Redox Mediators Bound with Flexible Chains to the Enzyme Surface," *J. Am. Chem. Soc.,* 113:1394–1397 (1991).

Schumm, et al., "Iterative Divergent/Convergent Approach to Linear Conjugated Oligomers by Successive Doubling of the Molecular Length: A Rapid Route to a 128 Å–Long Potential Molecular Wire," *Angew. Chem. Int. Ed. Engl.*, 33(11):1360–1363 (1994).

Sigal et al., "A Self–Assembled Monolayer for the Binding and Study of Histidine–Tagged Proteins by Surface Plasmon Resonance," *Anal. Chem.*, 68(3):490–497 (1996).

Southern, et al., "Arrays of complementary oligonucleotides for analysing the hybridisation behaviour of nucleic acids," *Nucleic Acids Research*, 22(8):1368–1373 (1994).

Strobel, S. A., et al., "Site–Specific Cleavage of a Yeast Chromosome by Oligonucleotide–Directed Triple–Helix Formation," *Science*, 249:73–75 (1990).

Su, et al., "Interfacial Nucleic Acid Hybridization Studied by Random Primer $^{32}$P Labelling and Liquid–Phase Acoustic Network Analysis," *Analytical Chemistry*, 66(6):769–777 (1994).

Telser, J., et al., "DNA Duplexes Covalently Labeled at Two Sites: Synthesis and Characterization by Steady–State and Time–Resolved Optical Spectroscopies," *J. Am. Chem. Soc.*, 111:7226–7232 (1989).

Telser, J., et al., "DNA Oligomers and Duplexes Containing a Covalently Attached Derivative of Tris(2,2'–bipyridine)ruthenium(II): Synthesis and Characterization by Thermodynamic and Optical Spectroscopic Measurements," *J. Am. Chem. Soc.*, 111:7221–7226 (1989).

Tour, "Conjugated Macromolecules of Precise Length and Constitution. Organic Synthesis for the Construction of Nanoarchitectures," *Chem. Rev.*, 96:537–553 (1996).

Tour, et al., "Self–Assembled Monolayers and Multilayers of Conjugated Thiols, α–ω–Dithiols, and Thioacetyl–Containing Adsorbates. Understanding Attachments between Potential Molecular Wires and Gold Surfaces," *J. Am. Chem. Soc.*, 117:9529–9534 (1995).

Tullius, T.D. and B.A. Dombroski, "Iron(II) EDTA Used to Measure the Helical Twist Along Any DNA Molecule," *Science*, 230:679–681 (1985).

Turro, N., et al. "Photoelectron Transfer Between Molecules Adsorbed in Restricted Spaces," *Photochem. Convers. Storage Sol. Energy, Proc. Int. Conf., 8th*, pp. 121–139 (1990).

Turro, N. J., et al., "Molecular Recognition and Chemistry in Restricted Reaction Spaces. Photophysics and Photoinduced Electron Transfer on the Surfaces of Micelles, Dendrimers, and DNA," *Acc. Chem. Res.*, 24:332–340 (1991).

Uosake, K., et al., "A Self–Assembled Monolayer of Ferrocenylalkane Thiols on Gold as an Electron Mediator for the Reduction of FE(III)–EDTA in Solution," *Electrochemica Acta.*, 36(11/12):1799–1801 (1991).

Van Ness, J., et al., "A Versatile Solid Support System for Oligodeoxynucleotide Probe–Based Hybridization Assays," *Nucleic Acids Research*, 19(12):3345–3349 (1991).

Weber, et al., "Voltammetry of Redox–Active Groups Irreversibly Adsorbed onto Electrodes. Treatment Using the Marcus Relation between Rate and Overpotential," *Anal. Chem.*, 66:3164–3172 (1994).

Williams, et al., "Studies of oligonucleotide interactions by hybridisation to arrays: the influence of dangling ends on duplex yield," *Nucleic Acids Research*, 22(8):1365–1367 (1994).

Winkler, J. R., et al., "Electron Transfer in Ruthenium-Modified Proteins," *Chem. Rev.*, 92:369–379 (1992).

Xu, et al., "Immobilization of DNA on an Aluminum(III) alkaneobisphosphonate Thin Film with Electrogenerated Chemiluminescent Detection," *J. Am. Chem. Soc.*, 116:8386–8387 (1994).

Xu, et al., "Immobilization and Hybridization of DNA on an Aluminum(III) Alkanebisphosphonate Thin Film with Electrogenerated Chemiluminescent Detection," *J. Am. Chem. Soc.*, 117:2627–2631 (1995).

Yang, et al., "Growth and Characterization of Metal(II) Alkaneobisphosphonate Multilayer Thin Films on Gold Surfaces," *J. Am. Chem. Soc.*, 115:11855–11862 (1993).

Zhou, et al., "Fluorescent Chemosensors Based on Energy Migration in Conjugated Polymers: The Molecular Wire Approach to Increased Sensitivity," *J. Am. Chem. Soc.*, 117:12593–12602 (1995).

Mucic et al., "Synthesis and Characterization of DNA with Ferrocenyl Groups Attached to their 5'–Termini: Electrochemical Characterization of a Redox–Acitve Nucleotide Monolayer," *Chem. Commun.*, pp. 555–557 (1996).

Carr et al., "Novel Electrochemical Sensors for Neutral Molecules," *Chem. Commun.*, 1649–1650 (1997).

Carter et al., "Voltammetric Studies of the Interaction of Metal Chelates with DNA. 2. Tris–Chelated Complexes of Cobalt(III) and Iron(II) with 10–Phenanthroline and 2,2'–Bipyridine," *J. Am. Chem. Soc.*, 11:8901–8911 (1989).

Johnston et al., "Trans–Dioxorhenium(V)–Mediated Electrocatalytic Oxidation of DNA at Indium Tin–Oxide Electrodes: Voltammetric Detection of DNA Cleavage in Solution," *Inorg. Chem.*, 33:6388–6390 (1994).

Korri–Youssoufi et al., "Toward Bioelectronics: Specific DNA Recognition Based on an Oligonucleotide–Functionalized Polypyrrole," *J. Am. Chem. Soc.*, 119(31):7388–7389 (1997).

Aizawa et al., "Integrated Molecular Systems for Biosensors," Sensors and Actuators B, B@$ (Nos 1/3) Part 1:1–5 (Mar. 1995).

Aizawa et al., "Integrated Molecular Systems for Biosensors," Sensors and Actuators B, B@$ (Nos 1/3) Part 1:1–5 (Mar. 1995).

Albers et al., "Design of Novel Molecular Wires for Realizing Long–Distance Electron Transfer," Biochemistry and Bioenergetics, 42:25–33 (1997).

Lincoln et al., "Shorting Circuiting the Molecular Wire," *J. Am. Chem. Soc.*, 119(6)1454–1455 (1997).

Velev et al., "In Situ Assembly of Colloidal Particles into Miniaturized Biosensors," The ACS Journal of Surfaces and Colloids, Langmuir, 15(11):3693–3698 (1999).

Blonder et al., "Three–dimensional Redox–Active layered Composites of Au–Au, Ag–Ag and Au–Ag Colloids," *Chem. Commun.* 1393–1394 (1998).

Mirkin et al., "A DNA–based Method for Ratioally Assembling Nonoparticles into Macroscopic Materials," *Nature*, 382:607–609 (1996).

Elghanian et al., "Selective Colorimetric Detection of Polynucleotides Based on the Distance–Dependent Optical Properties of Gold Nanoparticles," *Science*, 277:1078–1081 (1997).

Storhoff et al., "One–Pot Colorimetric Differentiation of Polynucleotides with Single Base Imperfections Using Gold Nanoparticles Probes," *J. Am. Chem. Soc.*, 120:1959–1964 (1998).

Watson et al., "Hybrid Nanoparticles with Block Copolymer Shell Structures," *J. Am. Chem. Soc.*, 121:462–463 (1999).

Mucic et al., "DNA–Directed Synthesis of Binary Nanoparticle Network Materials," J. Am. Chem. Soc., 120:12674–12675 (1998).

Mitchell et al., "Programmed Assembly of DNA Functionalized Quantum Dots," J. Am. Chem. Soc., 121:8122–8123 (1999).

Kamat et al., J. Phys. chem., 93(4):1405–1409 (1989). Abstract

Fotin, A. et al., "Parallel Thermodynamic Analysis of Duplexes on Oligodeoxyribonucleotide Microchips," Nucleic Acids Research, 216(6):1515–1521 (1998).

Guschin, D. et al., "Manual Manufacturing of Oligonucleotide, DNA, and Protein Microchips," Analytical Biochemistry, 250:203–211 (1997).

Dubiley, S. et al., "Factionation, phosphorylation and Ligation on Oligonucleotide Microchips to Enhance Sequencing by Hybridization," Nucleic Acids Research, 25(12):2259–2265 (1997).

Guschin, D. et al., "Oligonucleotide Microchips as Genosensors for Determinative and Environmental Studies in Microbiology," 63(6):2397–2402 (1997).

Drobyshev, A. et al., "Sequence Analysis by Hybridization with Oligonucleotide Microchip: Identification of β–thalassemia Mutations," Gene, 188:45–52 (1997).

Proudnikov, D. et al., "Chemical Methods of DNA and RNA Fluroescent Labeling," Nucleic Acids Research, 24(22):4535–4542 (1996).

Timofeev, E. et al., "Methidium Intercalator Inserted into Synthetic Oligonucleotides," Tetrahedron Letters, 37(47):8467–8470 (1996).

Livshits, M. et al., "Theoretical Analysis of the Kinetics of DNA Hybridization with Gel–Immobilized Oligonucleotides," Biophysical Journal, 71:2795–2801 (1996).

Timofeev, E. et al., "Regioselective Immobilization of Short Oligonucleotides to Acrylic Copolymer Gel," Nucleic Acids Research, 24(16): 3142–3148 (1996).

Parinov, S., "DNA Sequencing by Hybridization to Microchip octa– and Decanucleotide Extended by Stacked Pentanucleotides," Nucleic Acids Research, 24(15):2998–3004 (1996).

Yershov, G. et al., "DNA Analysis and Diagnostics on Oligonucleotide Microchips," Proc. Natl. Acad. Sci. USA, 93:4913–4918 (1996).

Mirzabkov, A. et al., "Dna Sequencing by Hybridization—a Megasequencing Method and a Diagnostic Tool," Tibtech, 12:27–32 (1994).

Brodolin, K. et al., "Conformational changes in E. Coli RNA Polymerase During Promoter Recognition," Nucleic Acids Research, 24(24):5748–5753 (1993).

Proudnikov, D. "Immobilization of DNA in Polyacrylamide Gel for the manufacture of DNA and DNA–Oligonucleotide Microchips," Analytical Biochemistry, 259:34–41 (1998).

Esipova, N.G. et al., "Investigation of Sites of Strong DNA–protein Interactions in DNA–binding Proteins by Theoretical and DNA–protein Cross–Linking Methods," Journal of Bimolecular Structure & Dynamics 12(6):A049 (1995).

Zimmermann et al., Nucleic Acids Research, 22:492–497.

Bain et al., J. Am. Chemical Soc. 111:7164–7175.

* cited by examiner

METALLIC SOLID SUPPORTS MODIFIED WITH NUCLEIC ACIDS

This is a continuation of application Ser. No. 08/808,750 filed Feb. 28, 1997 now abandoned and Ser. No. 08/475,051, filed Jun. 7, 1995, now U.S. Pat. No. 5,824,473.

FIELD OF THE INVENTION

The invention relates to metallic solid supports comprising blocking moieties and modified nucleic acids, and to methods of using them.

BACKGROUND OF THE INVENTION

The detection of specific nucleic acid sequences is an important tool for diagnostic medicine and molecular biology research. Gene probe assays currently play roles in identifying infectious organisms such as bacteria and viruses, in probing the expression of normal genes and identifying mutant genes such as oncogenes, in typing tissue for compatibility preceding tissue transplantation, in matching tissue or blood samples for forensic medicine, and for exploring homology among genes from different species.

Ideally, a gene probe assay should be sensitive, specific and easily automatable (for a review, see Nickerson, Current Opinion in Biotechnology 4:48–51 (1993)). The requirement for sensitivity (i.e. low detection limits) has been greatly alleviated by the development of the polymerase chain reaction (PCR) and other amplification technologies which allow researchers to amplify exponentially a specific nucleic acid sequence before analysis (for a review, see Abramson et al., Current Opinion in Biotechnology, 4:41–47 (1993)).

In contrast, specificity remains a problem in many currently available gene probe assays. The extent of molecular complementarity between probe and target defines the specificity of the interaction. Variations in the concentrations of probes, of targets and of salts in the hybridization medium, in the reaction temperature, and in the length of the probe may alter or influence the specificity of the probe/target interaction.

It may be possible under some limited circumstances to distinguish targets with perfect complementarity from targets with mismatches, although this is generally very difficult using traditional technology, since small variations in the reaction conditions will alter the hybridization. New experimental techniques for mismatch detection with standard probes include DNA ligation assays where single point mismatches prevent ligation and probe digestion assays in which mismatches create sites for probe cleavage.

Finally, the automation of gene probe assays is an area of high interest. Such assays generally rely on the hybridization of a labelled probe to a target sequence followed by the separation of the unhybridized free probe. This separation is generally achieved by gel electrophoresis or solid phase capture and washing of the target DNA, and is generally quite difficult to automate easily.

Immobilization of biomolecules on solid phases is widely used. Of particular interest is the immobilization of nucleic acids on solid surfaces for use in nucleic acid detection systems. There are a number of known techniques for the immobilization of nucleic acid on solid supports, including Hegner et al., FEBS Letters 336(3):452 (1993); Millan et al., Anal. Chem. 65:2317 (1993); Southern et al., Nucleic Acids Res. 22(8):1368 (1994); Maskos et al., Nucleic Acids Res. 20(7):1679 (1992); Palecek, Electroanalysis 8:7 (1996); Hashimoto et al., Anal. Chem. 66:3830 (1994); Su et al., Anal. Chem. 66(6):769 (1994); Chrisey et al., Nucleic Acids Res. 24(15):3031 (1996); Williams et al., Nucleic Acids Res. 22(8):1365 (1994); Xu et al., J. Am. Chem. Soc. 117:2627 (1995); Millan et al., Electroanalysis 4:929 (1994); Lee et al., Science 266:771 (1994); Millan et al., Anal. Chem. 66:2943 (1994); and Xu et al., J. Am. Chem. Soc. 116:8386 (1994).

It is an object of the present invention to provide novel compositions for the detection of nucleic acids, and methods of using the compositions.

SUMMARY OF THE INVENTION

In accordance with the objects outlined above, the present invention provides solid supports having a metallic surface. The metallic surface of the solid supports comprise blocking moieties, and at least one modified nucleic acid. The blocking moieties have at least a first and a second end, and is attached at the first end to the metallic surface. The modified nucleic acid comprises a linker moiety having a first and a second end. The first end of the linker moiety is attached to the solid support and the second end is attached to a nucleic acid.

In an additional aspect, the present invention provides solid supports having a metallic surface comprising a covalently immobilized monolayer, wherein a subset of the molecules forming the monolayer are covalently linked to nucleic acid.

In a further aspect the invention provides blocking moieties having the formula comprising:

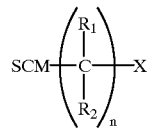

SCM is a sulfur-containing moiety which is attached to the metallic surface. $R_1$ and $R_2$ are independently selected from the group consisting of hydrogen and substituent groups, n is an integer from 3 to 50, and X is a terminal group.

In an additional aspect the invention provides modified nucleic acids having the formula comprising:

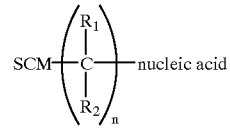

In a further aspect the invention provides solid supports having metallic surfaces comprising a mixed monolayer of blocking moieties and modified nucleic acids.

In an additional aspect, the invention provides methods of hybridizing probe nucleic acid to target nucleic acid. The methods comprise adding target nucleic acid to a solid support having a metallic surface comprising blocking moieties and modified nucleic acids as is described herein, under conditions where the probe nucleic acid and the target nucleic acid will hybridize to form a hybridization complex.

In a further aspect, the methods comprise additionally detecting the hybridization complex.

DETAILED DESCRIPTION OF THE INVENTION

The present invention is directed to the discovery that nucleic acids attached to metallic surfaces exhibit excellent characteristics in hybridization assays, in a stable, reproducible, rapid manner. That is, when a metallic surface such as gold is modified with nucleic acids, attached via linkers, and blocking moieties, which serve to shield the nucleic acids from the metallic surface, excellent hybridization characteristics are seen. Thus, the present invention provides new and useful compositions for the immobilization of nucleic acids on solid supports.

Accordingly, the present invention provides metallic solid supports comprising blocking moieties and modified nucleic acids.

By "solid support comprising a metallic surface" or grammatical equivalents herein is meant a surface that has a metallic layer. Suitable metallic layers include any metals to which thiol groups may be attached, with gold and copper being preferred, and gold being particularly preferred. Thus, any material which can be made to contain a metallic layer or film can be used as a solid support. Accordingly, the entire surface may be metal, or only a thin layer or film of metal on the top of a different material may be used. Thus, for example, glass, plastic, polymers, graphite, or metals other than gold and copper can be used as a support, with at least a portion of one side of the support having a metallic surface.

The deposition of gold onto any number of materials is known, using techniques including vapor deposition, electroplating, sputter coating, and chemical deposition. In addition, the surface can be polished as is known in the art.

The metallic solid supports described herein are generally depicted as a flat surface, which is only one of the possible conformations of the metallic solid support and is for schematic purposes only. In addition, the metallic surface on the solid support may be a single continguous surface, or may be divided up into smaller locations, in any number of ways. That is, the metallic solid supports can be used to form arrays, where different regions ("addresses") on the surface contain different nucleic acids. As will be appreciated by those in the art, this may be done in a variety of ways. In one embodiment, the different addresses are physically separated by areas that do not contain a metallic layer. Alternatively, the different addresses may be separated by the addition of other materials, such as polymers, glass, silicon and other materials to the metallic layer. Alternatively, the different addresses are merely separated by location.

Blocking moieties are covalently attached to the metallic solid supports described herein. "Blocking moieties" are molecules which are covalently attached to the metallic solid support that function to shield the nucleic acids from the metallic surface. For the purposes of this invention, the attachment of a sulfur moiety to a metallic surface, such as gold, is considered covalent.

In general, blocking moieties have at least a first and a second end. The first end is used to covalently attach the blocking moiety to the metallic solid support. The second end terminates in a terminal group, defined below. However, in some embodiments, the blocking moieties may be branched molecules. Thus, for example, the first end is used for attachment to the solid support and all or some of the other ends may terminate in a terminal group, as defined below.

In a preferred embodiment, the blocking moieties have the formula shown in Formula 1:

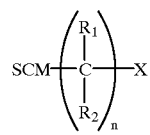

Formula 1

In Formula 1, SCM is a sulfur-containing moiety, $R_1$ and $R_2$ are independently selected from the group consisting of hydrogen and substituent groups, n is an integer from 3 to 50 and X is a terminal group.

By "sulfur-containing moiety" or SCM, herein is meant a group that contains a sulfur atom which may be used to attach the blocking moiety at one end to the metallic solid support. Suitable sulfur-containing moieties include, but are not limited to, thiols (-SH) and disulfides (-S-S-R; for example, the blocking moieties may be made as "dimers", attached via disulfides, for attachment to the metallic surface). In a preferred embodiment, the sulfur-containing moiety is a thiol. Upon attachment to the metallic surface, the hydrogen atom is removed, leaving only the sulfur atom attached to the surface.

$R_1$ and $R_2$ are independently hydrogen or a substituent group. That is, $R_1$ and $R_2$ may be the same, or different, and R substituents on each carbon may be the same or different as on adjacent carbon atoms. By "substituent group" herein is meant any one of a number of moieties which may be attached to the blocking moieties. These R groups may be added to alter the packing of the blocking and linker moieties on the metallic surface, to alter the hydrophobicity or hydrophilicity of the blocking and linker moieties, to alter the flexibility, i.e. the rotational, torsional, or longitudinal flexibility of the blocking or linker moieties, or to increase the stability of the monolayer via interchain interactions. Preferred $R_1$ and $R_2$ groups are hydrogen. Suitable substituent groups include, but are not limited to, alkyl, aryl, amino, nitro, ether, ester, halogen, aldehyde, alcohol, ethylene glycol, amido, phosphorus containing moieties and silicon containing moieties.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1–C30), with a preferred embodiment utilizing from about 1 to about 20 carbon atoms (C1–C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, phosphorus and silicone being preferred. Sulfur is generally not preferred, due to the possibility of interaction with the metallic surface. Alkyl includes substituted alkyl groups. By "substituted alkyl group" herein is meant an alkyl group further comprising one or more substitution moieties "R", as defined above.

By "aryl group" or grammatical equivalents herein is meant an aromatic monocyclic or polycyclic hydrocarbon moiety generally containing 5 to 14 carbon atoms (although larger polycyclic rings structures may be made) and any carbocyclic ketone or thioketone derivative thereof, wherein the carbon atom with the free valence is a member of an aromatic ring. Aromatic groups include arylene groups and aromatic groups with more than two atoms removed. For the purposes of this application aromatic includes heterocycle. "Heterocycle" or "heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes thienyl, furyl, pyrrolyl, pyrimidinyl, oxalyl, indolyl, purinyl, quinolyl, isoquinolyl, thiazolyl, imidozyl, benzoazole, etc. Aryl includes substituted aryl, wherein the aryl group further comprises one or more substitution moieties "R", as defined above.

By "amino groups" or grammatical equivalents herein is meant —$NH_2$, —NHR and —$NR_2$ groups, with R being as defined herein.

By "nitro group" herein is meant an —$NO_2$ group.

By "phosphorus containing moieties" herein is meant compounds containing phosphorus, including, but not limited to, phosphines and phosphates. By "silicon containing moieties" herein is meant compounds containing silicon. By "ether" herein is meant an —O—R group. By "ester" herein is meant a —COOR group. By "carboxyl" herein is meant—COOH.

By "halogen" herein is meant bromine, iodine, chlorine, or fluorine. Preferred substituted alkyls are partially or fully halogenated alkyls such as $CF_3$, etc.

By "aldehyde" herein is meant —RCOH groups.

By "alcohol" herein is meant —OH groups (also referred to herein as "hydroxyl" groups), and alkyl alcohols —ROH.

By "amido" herein is meant —RCONH— or RCONR— groups.

By "ethylene glycol" herein is meant a —(O—$CH_2$—$CH_2$)$_n$— group, although each carbon atom of the ethylene group may also be singly or doubly substituted, i.e. —(O—$CR_2$—$CR_2$)$_n$—, with R as described above. Ethylene glycol derivatives with other heteroatoms in place of oxygen (i.e. —(N—$CH_2$—$CH_2$)$_n$— or —(S—$CH_2$—$CH_2$)$_n$—, or with substitution groups) are also preferred.

Preferred substitution groups include, but are not limited to, amido, ethylene glycol, and alkyl groups of 1 to 10 carbon atoms.

The second end of the blocking moiety terminates in a terminal group. By "terminal group", or "terminal moiety" herein is meant a chemical group at the terminus of the blocking moiety. The terminal groups may be chosen to modulate the interaction between the nucleic acid and the blocking moieties, or the surface. Thus, for example, in a preferred embodiment, when the blocking moieties form a monolayer as is generally described below, the terminal group may be used to influence the exposed surface of the monolayer. Thus, for example, the terminal group may be neutral, charged, or sterically bulky. For example, the terminal groups may be negatively charged groups, effectively forming a negatively charged surface such that when the probe or target nucleic acid is DNA or RNA the nucleic acid is repelled or prevented from lying down on the surface, to facilitate hybridization. This may be particularly useful when the nucleic acid attached to the metallic surface via a linker moiety is long.

The terminal groups may be all the same, or different. That is, the blocking moieties attached to metallic supports may have the same terminal groups, or two or more of the terminal groups may be different.

Suitable terminal groups include, but are not limited to, hydrogen, alkyl, amino, carboxyl, hydroxyl, and amido. Preferred terminal groups include hydrogen and hydroxyl, with hydroxyl being particularly preferred.

The length of the blocking moieties will vary. In general, n is an integer from 3 to 50, although longer blocking moieties may be used in some situations. Without being bound by theory, it appears that for efficient hybridization of nucleic acids on a surface, the hybridization should occur at a distance from the surface, i.e. the kinetics of hybridization increase as a function of the distance from the surface, particularly for long oligonucleotides of 200 to 300 basepairs. Accordingly, the length of the blocking moiety (and linker moieties) is such that the closest nucleotide of the nucleic acids described herein are positioned from about 6 Å to about 100 Å (although distances up to 500 Å may be used) from the metallic solid support, with from about 20 Å to about 60 Å being preferred. Accordingly, n will generally be from about 3 to 50, with from about 6 to about 24 being preferred, and 12 to 18 being particularly preferred.

It should also be noted that blocking and linker moieties containing heteroatoms in the backbone may be used. Suitable heteroatoms include, but are not limited to, oxygen, nitrogen, phosphorus, and silicon. In some embodiments, sulfur heteroatoms may be used, although this is generally not preferred as this may result in incorrect attachment to the metallic surface.

All of the blocking moieties attached to a metallic surface may be the same, or at least two of the blocking moieties are different. Thus, for example, when the blocking moieties have the structure shown in Formula 1, some blocking moieties may be one length (for example, n=12) and others may be a different length (n=16). Alternatively, some blocking moieties may have substitutent groups and others none or different substituent groups.

In addition to the blocking moieties, the metallic solid supports of the invention comprise modified nucleic acids. By "nucleic acids" or "oligonucleotides" herein is meant at least two nucleotides covalently linked together. A nucleic acid of the present invention will generally contain phosphodiester bonds, although in some cases, as outlined below, a nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate, phosphorodithioate, O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). These modifications of the ribose-phosphate backbone may be done to facilitate the addition of electron transfer moieties, or to increase the stability and half-life of such molecules in physiological environments.

Particularly preferred are peptide nucleic acids (PNA). This backbone is substantially non-ionic under neutral conditions, in contrast to the highly charged phosphodiester backbone of naturally occurring nucleic acids. This results in two advantages. First, this backbone exhibits improved hybridization kinetics. PNAs have larger changes in the melting temperature (Tm) for mismatched versus perfectly matched basepairs. DNA and RNA typically exhibit a 2–4° C. drop in Tm for an internal mismatch. With the non-ionic backbone of PNA, the drop is closer to 7–9° C. This may allow better detection of mismatches. Similarly, due to their non-ionic nature, hybridization of the bases attached to these backbones is relatively insensitive to salt concentration.

The nucleic acids may be single stranded or double stranded, as specified, or contain portions of both double stranded or single stranded sequence. In a preferred embodiment, probe nucleic acids are single stranded. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine and hypoxathanine, etc. As used herein, the term "nucleotide" includes nucleosides.

The nucleic acids of the invention may also be characterized as "probe" nucleic acids and "target," nucleic acids. These terms are known in the art. Either probe or target nucleic acids maybe attached to the solid support via linkers. In a preferred embodiment, the probe nucleic acids are attached, via linker moieties, to the solid support, and the target nucleic acids are added in solution. As outlined below, one or both of the probe and target nucleic acids may be labelled.

Probe nucleic acids or probe sequences are preferably single stranded nucleic acids. The probes of the present invention are designed to be complementary to the target sequence, such that hybridization of the target sequence and the probes of the present invention occurs. This complementarity need not be perfect; there may be any number of base pair mismatches which will interfere with hybridization between the target sequence and the single stranded probe nucleic acids of the present invention. However, if the number of mutations is so great that no hybridization can occur under even the least stringent of hybridization conditions, the sequence is not a complementary target sequence.

As is appreciated by those in the art, the length of the probe will vary with the length of the target sequence and the hybridization and wash conditions. Generally, oligonucleotide probes range from about 8 to about 50 nucleotides, with from about 10 to about 30 being preferred and from about 12 to about 25 being especially preferred. In some cases, very long probes may be used, e.g. 50 to 200–300 nucleotides in length.

Target nucleic acids or sequences means a nucleic acid sequence on a single strand of nucleic acid. The target sequence may be a portion of a gene, a regulatory sequence, genomic DNA, cDNA, mRNA, or others. It may be any length, with the understanding that longer sequences are more specific. As is outlined herein, probes are made to hybridize to target sequences to determine the presence or absence of the target sequence in a sample. Generally speaking, this term will be understood by those skilled in the art. Target nucleic acids may be prepared or amplified as is generally known in the art, and more fully described below. When target nucleic acids are attached to the metallic surface, they will generally be the same size as outlined for probe nucleic acids, above.

The nucleic acids of the invention are modified with linker moieties, to form modified nucleic acids which are attached to the metallic surface. By "modified nucleic acid" herein is meant a nucleic acid as defined above covalently attached to a linker moiety.

By "linker moieties" or grammatical equivalents, herein is meant molecules which serve to immobilize the nucleic acid at a distance from the metallic support. Linker moieties have a first and a second end. Branched linker moieties are not preferred. The first end is used to covalently attach the linker moiety to the metallic solid support. The second end is used for attachment to the nucleic acid.

In a preferred embodiment, the linker moieties have the formula shown in Formula2:

Formula 2

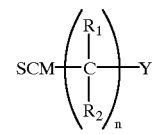

In Formula 2, SCM is a sulfur-containing moiety, as defined above. $R_1$ and $R_2$ are independently selected from the group consisting of hydrogen and substituent groups, n is an integer as defined above for blocking moieties, and Y is the point of attachment for the nucleic acid. Y may be a bond, an atom or an attachment moiety used to attach the nucleic acid to the linker atom, as is more fully described below. Accordingly, in a preferred embodiment, the modified nucleic acid of the invention have the formula depicted below in Formula 3:

Formula 3

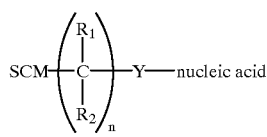

In Formula 3, the nucleic acid is preferably a probe nucleic acid as defined herein.

As for the blocking moieties, the linker moieties attached to a single metallic support may be all the same, or at least two of them may be different. In addition, the blocking moieties and the linker moieties may be the same, or different. That is, in a preferred embodiment, the blocking moieties and the linker moieties are the same (except for the nucleic acids and terminal groups). That is, the structure of the —$(CR_1R_2)_n$— portion of the blocking and linker moieties are the same. Alternatively, the blocking moieties and the linker moietes are different (i.e. the blocking and linker moieties have different—$(CR_1R_2)_n$— portions), as is outlined below.

In a preferred embodiment, the blocking moieties, together with the modified nucleic acids, form a monolayer (sometimes referred to as a self-assembled monolayer (SAM)), as is generally understood by those in the art. The formation of a monolayer may be determined in several ways, as is appreciated by those in the art. The presence of a monolayer on at least a portion of the surface may be determined as is known in the art, for example by using ellipsometry, X-ray photoelectron spectroscopy, infrared external reflectance spectroscopy, or surface plasmon resonance.

As outlined above, in this embodiment, the blocking moieties and linker moieties may be the same, or different. Thus, for example, blocking moieties may be used with a certain length (n=16), with linker moieties being either the same length, shorter or longer. A preferred embodiment utilizes linker moieties that are slightly longer, such that the probe nucleic acids do not rest right on the surface of the monolayer, but rather are some distance away.

Without being bound by theory, it appears that densely packed probe nucleic acids generally do not result in good hybridization with target nucleic acids. Accordingly, the ratio of blocking moiety to modified nucleic acid generally ranges from about 50:1 to 100,000:1, with from about 100:1 to 1000:1 being preferred and from about 100:1 to 500:1 being especially preferred.

The compositions of the invention are generally synthesized as outlined below, generally utilizing techniques well known in the art.

The blocking moieties are made as follows, using techniques well known in the art. When $R_1$ and $R_2$ are hydrogen, the blocking moieties can be made in several ways, starting with a commercially available alkyl chain, OH—$(CH_2)_n$—COOH. The first step for all methods involves the replacement of the hydroxyl group with a bromine to form Br—$(CH_2)_n$—COOH. In one embodiment, the carboxyl group is reduced to a hydroxyl to form Br—$(CH_2)_n$—OH, and then the bromine is replaced with a protected sulfur (PS) to form PS—$(CH_2)_n$—OH, where the hydroxy is the terminal group. Additional terminal groups may be made using the hydroxyl group as a functional group for the attachment of other terminal groups, as is generally known in the art. In a second embodiment, the Br—$(CH_2)_n$—OH reaction product is reacted with a protected sulfur to form Br—$(CH_2)_n$—PS, where the bromine can then be exchanged for other terminal groups as will be appreciated by those in the art.

When R1 and R2 substituents are used, generally shorter alkyl groups with reactive functional groups are used to add substituents groups while creating longer chains, as will be appreciated by those in the art.

Generally, the blocking and linker moieties are generated with protected sulfur-containing moieties. Protecting groups are known in the art; see for example Hsung et al., Tetrahedron Lett. 36(26):4525 (1995), hereby incorporated by reference in its entirety. The protecting groups are removed prior to attachment to the solid support, as outlined below.

The linker moieties are made as outlined above for blocking moieties. Thus, the first end of the linker moieties contains a sulfur-containing moiety, generally protected for subsequent attachment to the metallic surface. The second end of the linker moiety is made containing a functional group or an attachment group that will allow the attachment of nucleic acids. This is generally done using modified nucleotides, described below, which are incorporated into nucleic acids. The nucleic acid containing the modified nucleotide is then reacted with the attachment group, to form a covalent bond between the linker moiety and the nucleic acid, resulting in a modified nucleic acid.

Suitable attachment groups include carboxy, hydroxy, amino and phosphate groups.

In a preferred embodiment, the linker moieties are attached to a nucleotide in a number of positions. In a preferred embodiment, the linker moieties are attached at the 2' or 3' position on the ribose, with 2' being particularly preferred. In a preferred embodiment, the linker moieties are attached via a phosphate linkage. Alternatively, the linker moieties may be added to a terminal base.

In one embodiment, the linker moieties are added to the bases of the terminal nucleosides. Thus, when the target sequence to be detected is m nucleosides long, a probe can be made which has an extra terminal nucleoside at one or both of the ends of the nucleic acid (m+1 or m+2), which are used to covalently attach the electron transfer moieties but which do not participate in basepair hybridization. This extra terminal nucleoside is important since attachment of moieties to an internal nucleoside base is expected to perturb Watson-Crick basepairing. That is, the base used for covalent attachment should be outside of the region used to identify the target sequence.

The present invention further provides methods for the site-specific addition of linker moieties to nucleic acids. As outlined above, the linker moieties may be added at the 2' or 3' position of a ribose of the ribose-phosphate backbone, to a 3' or 5' terminal base, or to an internal nucleoside using peptide nucleic acid linkages, phosphoramidate bonds, phosphorothioate bonds, phosphorodithioate bonds, or O-methyl phosphoramidate bonds.

For attachment to a ribose, a preferred embodiment utilizes modified nucleosides to attach the linker moieties. Preferably amino-modified nucleosides and nucleotides are used. In an alternate embodiment, thio-modified nucleosides are used to attach the linker moieties to the nucleic acids.

The modified nucleosides are then used to site-specifically add a linker moiety, either to the 3' or 5' termini of the nucleic acid, or to any internal nucleoside. Either the 2' or 3' position of the ribose may be altered for attachment at the 3' terminus; for attachment to an internal ribose or the 5' terminus, the 2' position is preferred. Thus, for example, the 2' position of the ribose of the deoxyribo- or ribonucleoside is modified prior to the addition of the linker moiety, leaving the 3' position of the ribose unmodified for subsequent chain attachment if necessary. In a preferred embodiment, an amino group is added to the 2' or 3' carbon of the sugar using established chemical techniques. (Imazawa et al., J. Org. Chem., 44:2039 (1979); Hobbs et al., J. Org. Chem. 42(4) :714 (1977); Verheyden et al. J. Org: Chem. 36(2):250 (1971)). Eckstein et al., Oligonucleotides and Analogues, A Practical Approach, IRL Press, 1991.

The amino-modified nucleosides made as described above are converted to the 2' or 3' modified nucleotide triphosphate form using standard biochemical methods (Fraser et al., Proc. Natl. Acad. Sci. USA, 4:2671 (1973)).

Modified nucleosides for the attachment of the linker moieties to the bases, is done as outlined in Telser et al, J. Am. Chem. Soc. 111:7221 (1989), and Telser et al., J. Am. Chem. Soc. 111:7226 (1989), both of which are expressly incorporated by reference. These modified nucleosides are then incorporated at either the 3' or 5' terminus as outlined below.

Once the modified nucleosides are prepared, protected and activated, they may be incorporated into a growing oligonucleotide by standard synthetic techniques (Gait, Oligonucleotide Synthesis: A Practical Approach, IRL Press, Oxford, UK 1984; Eckstein, supra) in several ways. In one embodiment, one or more modified nucleosides are incorporated into a growing oligonucleotide chain by using standard molecular biology techniques such as with the use of the enzyme DNA polymerase I, T4 DNA polymerase, T7 DNA polymerase, Taq DNA polymerase, reverse transcriptase, and RNA polymerases. For the incorporation of a 3' modified nucleoside to a nucleic acid, terminal deoxynucleotidyltransferase may be used. (Ratliff, Terminal deoxynucleotidyltransferase. In The Enzymes, Vol 14A. P. D. Boyer ed. pp 105–118. Academic Press, San Diego, Calif. 1981). Alternatively, and preferably, the amino nucleoside is converted to the phosphoramidite or H-phosphonate form, which are then used in solid-phase or solution syntheses of oligonucleotides. In this way the modified nucleoside, either for attachment at the ribose (i.e. amino- or thiol-modified nucleosides) or the base, is incorporated into the oligonucleotide at either an internal position or the 5' terminus. This is generally done by protecting the 5' position of the ribose with 4',4-dimethoxytrityl (DMT) followed by reaction with 2-cyanoethoxy-bis-diisopropylaminophosphine in the presence of diisopropylammonium tetrazolide to give the phosphoramidite as is known in the art; although other techniques may be used as will be appreciated by those in the art. See Gait, supra; Caruthers, Science 230:281 (1985), both of which are expressly incorporated herein by reference.

For attachment of a linker moiety to the 3' terminus, a preferred method utilizes the attachment of the modified nucleoside to controlled pore glass (CPG) or other polymeric supports. In this embodiment, the modified nucleoside is protected at the 5' end with DMT, and then reacted with succinic anhydride with activation. The resulting succinyl compound is attached to CPG or other polymeric supports as is known in the art. Further phosphoramidite nucleosides are added, either modified or not, to the 5' end after deprotection.

In other embodiments, the linker moieties are added to the middle of the nucleic acid, i.e. to an internal nucleoside. This may be accomplished in three ways.

In a preferred embodiment, a modified nucleoside is incorporated at the 5' terminus as described above. In this embodiment, oligonucleotide synthesis simply extends the 5' end from the modified nucleoside using standard techniques. This results in an internally amino modified oligonucleotide.

In an alternate embodiment, linker moieties are added to the backbone at a site other than ribose, resulting in an internal attachment. For example, phosphoramide rather than phosphodiester linkages can be used. While structural deviations from native phosphodiester linkages do occur and have been studied using CD and NMR(Heller, Acc. Chem. Res. 23:128 (1990); Schuhmann et al. J. Am. Chem. Soc. 113:1394 (1991)), the phosphoramidite internucleotide link has been reported to bind to complementary polynucleotides and is stable (Beaucage et al., supra, and references therein; Letsinger, supra; Sawai, supra; Jager, Biochemistry 27:7237 (1988)). In this embodiment, dimers of nucleotides are created with phosphoramide linkages at either the 2'-5' or 3'-5' positions. A preferred embodiment utilizes the 3'-5' position for the phosphoramide linkage, such that structural disruption of the subsequent Watson-Crick basepairing is minimized. These dimer units are incorporated into a growing oligonucleotide chain, as above, at defined intervals, as outlined below.

Thus, the present invention provides methods for making a nucleic acid with covalently attached linker moieties. In a preferred embodiment, the method is for making a nucleic acid with a linker moiety attached at the 3' terminus of the nucleic acid. The method comprises attaching a 2'-amino modified nucleoside to control pore glass, and adding phosphoramidite nucleosides to the 5' terminus of the modified nucleoside to form a nucleic acid. The nucleic acid is then optionally cleaved from the CPG using known methods. The linker moiety is then added to the 2'-amino modified nucleoside.

In a preferred embodiment, methods for making a nucleic acid with a linker moiety attached at the 5' terminus are provided. The method comprises attaching a nucleoside to control pore glass, and adding phosphoramidite nucleosides to the 5' terminus of the nucleoside to form a nucleic acid. A 2' or 3' amino modified nucleoside is added to the 5' terminus, and the nucleic acid is optionally cleaved from the CPG. The linker moiety is added to the 2' or 3'-amino modified nucleoside.

The cleavage from the CPG may occur either prior to linker addition or afterwards.

In a further embodiment for the modification of internal residues, 2' or 3' modified nucleoside triphosphates are generated using the techniques described above for the 3' nucleoside modification. The modified nucleosides are inserted internally into nucleic acid using standard molecular biological techniques for labelling DNA and RNA. Enzymes used for said labelling include DNA polymerases such as polymerase I, T4 DNA polymerase, T7 DNA polymerase, Taq DNA polymerase, reverse transcriptase and RNA polymerases such as *E. coli* RNA polymerase or the RNA polymerases from phages SP6, T7 or T3 (Short Protocols in Molecular Biology, 1992. Ausubel et al. Ed. pp 3.11–3.30).

As described above, the linker moiety may be attached to any of the five bases (adenine, thymine, uracil, cytosine, guanine and other non-naturally occurring bases such as inosine, xanthine, and hypoxanthine, among others). This is done using well known techniques; see Telser et al., J. Am. Chem. Soc. 111:7226–7232 (1989); Telser et al., J. Am. Chem. Soc. 111:7221–7226 (1989). As outlined herein, these terminally modified nucleosides may be attached to the nucleic acid enzymatically as is known in the art, using DNA polymerases; alternatively, the modified nucleosides may be incorporated into a growing oligonucleotide chain using traditional phosphoramidite chemistry during oligonucleotide synthesis as is outlined herein.

Thus, nucleic acids containing modified nucleotides are generated. The modified nucleotides are then used to add linker moieties to form modified nucleic acids as follows. When the modified nucleotide is an amino-modified nucleotide, a linker moiety containing a terminal carboxy group can be added, such that an amide bond is formed.

In a preferred embodiment, linker moieties are added without modified nucleotides. As outlined in the examples, a phosphoramidite moiety may be added to the linker moieties. The modified linker moieties are then added, using standard methods, to a nucleic acid.

Once the components are synthesized, the components are attached to the metallic solid support in a variety of ways. In a preferred embodiment, the blocking moieties are added first to the metallic solid support, followed by the addition of the modified nucleic acids. Alternatively, modified nucleic acids may be added first. Similarly, the modified nucleic acids and the blocking moieties may be added simultaneously. Alternatively, in any of the above embodiments, linker moieties without attached nucleic acids are attached to the surface, followed by the addition of the nucleic acid. A preferred embodiment utilizes mixtures of blocking moieties and modified nucleic acids, added in ratios from 100:1 to 500:1 of blocking moiety:modified nucleic acid, to the surface. The mixture is applied to the surface with heat, generally ranging from 50–70° C., for several hours.

Addition of sulfur-containing moieties to metallic surfaces is well known in the art, and generally involves the removal of the sulfur-protecting group followed by contact with the metal.

Once made, the compositions find use in a number of applications, as described herein.

In a preferred embodiment, the compositions are useful in methods of assaying for the presence or absence of target nucleic acids. Thus, the present invention provides methods of hybridizing probe nucleic acids to target nucleic acids. The methods comprise adding or contacting target nucleic acids to a metallic solid support of the invention. As outlined above, the metallic solid support comprises blocking moieties, and modified probe nucleic acids. The contacting is done under conditions where the probe and target nucleic acids, if suitably complementary, will hybridize to form a double-stranded hybridization complex.

The assay conditions may vary, as will be appreciated by those in the art, and include high, moderate or low stringency conditions as is known in the art; see for example Maniatis et al., Molecular Cloning: A Laboratory Manual, 2d Ed., 1989; and Short Protocols in Molecular Biology, ed. Ausubel, et al. The assays may be done at a variety of temperatures, and using a variety of incubation times, as will be appreciated by those in the art. In addition, a variety of other reagents may be included in the hybridization assay, including buffers, salts, proteins, detergents, etc. Positive and negative controls are generally run.

A distinct advantage of the present invention over the prior art is the lack of blocking and minimal washing steps that are required. Generally, the attachment of probe nucleic acids to a solid support such as nitrocellulose requires that after addition of the probe nucleic acids, remaining attachment sites on the support must be blocked, for example with albumin protein or salmon sperm DNA, to prevent non-specific target nucleic acid binding. However, these blocking steps are unnecessary in the present invention, since non-specific binding to the metallic surface or monolayer is extremely low.

In a preferred embodiment, the method further comprises washing or rinsing any non-bound target nucleic acid off the metallic surface.

In a preferred embodiment, the methods further comprise the step of detecting the hybridization complex. As will be appreciated by those in the art, this may be done in a wide variety of ways.

In a preferred embodiment, the target nucleic acid is labelled to facilitate detection. By "labelled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position. Current hybridization assays use a wide variety of labels, with radioisotopes and fluorescent molecules being particularly preferred. Thus, detection of the hybridization complex is done by the detection of the presence of the label; the presence of a signal indicates that the hybridization complex is present. The exact detection mechanism will depend on the composition of the label, as will be appreciated by those in the art. Preferred detection modes include fluorescence and atomic or chemical force microscopy.

In an alternative embodiment, the target nucleic acid is not labelled, but an agent that distinguishes between single- and double-stranded nucleic acids, such as intercalating agents, is used. For example, detectable molecules that preferentially intercalate into the double-stranded hybridization complex, rather than bind to single-stranded nucleic acid, can also be used to detect the hybridization complexes.

Alternatively, detection may be via atomic or chemical force microscopy, as is generally described in Meade et al., Binding Forces Between Complementary DNA Strands in Chemical Force Microscopy, submitted for publication, or surface plasmon resonance.

Thus, the present invention provides compositions and assays useful in nucleic acid detection, and thus find use in a variety of research and clinical applications. For example, the novel nucleic acid compositions may be used in genetic diagnosis, viral and bacterial detection systems, forensic DNA analysis, sequencing by hybridization, mutation detection, etc.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Preparation of a Hydroxythiol for Attachment to a Gold Electrode $OH(CH_2)_{16}OH$ was purchased from Aldrich and the monoacetate form prepared by slurring the material in dry $CH_2Cl_2$. 0.5 equiv. of dimethylaminopyridine was added along with 1.4 equivalents of triethylamine and 1 equivalent of acetic anhydride. The reaction was allowed to proceed for 2 hours and purified by flash chromatography (80:20 hexane:diethyl ether. The monoacetate compound was converted to the monotosylate-monoacetate using p-TSOCl by literature procedures and then treated with triphenyl methylmercaptan. To remove the monoacetate, the product was dissolved in MeOH (1 mmol, 9 ml), cooled to 0° C., and aqueous solution of NaOH (1 mmol, in 2 ml water) added. The temperature was allowed to rise to room temperature slowly, and the reaction followed by TLC (5% MeOH/$CH_2Cl_2$). When the ester was gone the mixture was recooled to 0° C., and acidified with $KHSO_4$ to pH 5–6 using pH paper. The MeOH was evaporated, and the residue was extracted with $CH_2Cl_2$ (200 ml), dried ($Na_2SO_4$), evaporated and checked via TLC. The material was phosphoroamidited by standard procedures. This material was inserted into the DNA synthesizer and an modified oligonucleotide produced. The phosphoramidited oligonucleotide was modified with a ruthenium complex by adding $Ru(bpy)_2CO_3$ followed by imidazole to yield a $Ru(bpy)_2im$ oligonucleotide. The trityl protecting group was removed by dissolving the nucleotide in 200 $\mu$l of 0.1 M triethylammonium acetate (TEAA) buffer, pH 7.5. 30 $\mu$l of 1 M silver nitrate solution was added and the mixture vortexed and incubated at room temperature for 30 minutes. 50 $\mu$ of 1 M dithiothritol (DTT) was added, the mixture vortexed and incubated for 15 minutes, at which point it was microcentrifuged for 15 minutes to remove precipitated Ag+DTT. The supernatant was collected and the pellet was washed with 100 $\mu$l of TEAA buffer and the solutions pooled. The resulting oligonucleotide was then attached to the gold surface by standard techniques.

Example 2

Synthesis of a Mixed Monolayer

A self-assembled monolayer of modified nucleic acids and $C_{16}$ blocking moieties with hydroxyl terminal groups was made.

Materials. All materials were of reagent grade and thoroughly dried by standard techniques. Water was deionized with Barnstead NANOpure II filtration unit to 18 MΩ·cm resistivity.

Synthesis if SH(CH$_2$)$_{16}$O-oligonucleotides. 2.05 gr. (7.93×10$^{-3}$ moles of HO(CH$_2$)$_{16}$OH was placed in a 100 ml round bottom flask and 60 ml of CH$_2$Cl$_2$ added along with 0.05 equiv. of DMAP and 1.4 equiv. of triethylamine and 0.695 mls of acetic anhydride. The reaction was monitored by TLC (silica gel: Kieselgel 60 F$_{254}$EM science: mobile phase 50/50 diethyl ether/hexane: CAM stain). The starting diol (R$_f$=0.05) and diacetate (R$_f$=0.7) were separated from the desired produce (65% yield, R$_f$32 0.25) by flash chromatography (Silica gel 60, EM Science: mobile phase 80/20 hexane ether). The $^1$H and $^{13}$C NMR, and mass spectrum were consistent with the expected product.

0.5 gr. (1.7 m moles) of the monoacetate protected diol [HO(CH$_2$)$_{16}$)OCH$_3$] was slurried in 25ml of dry pyridine and cooled to 4° C. TosCl (0.634 gr. 33 m moles) was added with stirring and the reaction allowed to proceed for 36 hr. at 4° C., and an additional 2 hr. at room temperature. The solution was poured into a beaker containing 200 ml of ice water with stirring and filtered. The recovered solid was washed with water, dissolved in pet ether, and charcoal added. After filtration, the solution was rotovaped to dryness. TLC revealed the desired product (R$_f$=0.58) and the material was purified by flash chromatography. The $^1$H and $^{13}$C NMR, and mass spectrum were consistent with the expected product.

0.37 gr (0.81 m moles) of the tosylated material [TOS—O(CH$_2$)$_{16}$)OCH3] was dissolved in 10 ml of DMF and thoroughly degassed on a vacuum line. 1.1 equiv. of Triphenylmethylmercaptan (TPMM, Aldrich) was dissolved in 5 ml of previously degassed ethanol. NaOH (1.05 equiv.) was dissolved in 150 µl of water and added via syringe to the TPMM solution and this solution was cannulated into the DMF solution under positive pressure Ar. The reaction was allowed to proceed for 12 hr and TLC revealed two products: R$_f$=0.4 and 0.84. The materials were confirmed to the desired product (R$_f$=0.84) and the product without the acetate protecting group (R$_f$=0.4). The deacylated material [TrS(CH$_2$)$_{16}$)OH] was purified by flash chromatography (80/20) hexane:diethyl ether) and thoroughly dried. The $^1$H and $^{13}$C NMR, and mass spectrum were consistent with the expected product.

220 mg. (0.44 m moles) of [TrS(CH$_2$)$_{16}$)OH] was slurried in 15 ml of dry CH$_2$Cl$_2$ and immediately 325 ul of DIEA added. 145 ul of 2-cyanoethyl N,N-disopropylchlorophosphoramidite was added dropwise via syringe over a period of 5 min. The reaction was allowed to proceed for 30 min. and an additional 50 ul of the phosphoramidite was added. TLC (mobile phase: 50:50:1, hexane:diethyl ether:TEA) revealed the desired product R$_f$=72 (ninhydrin stain). The material was purified by flash chromatography (mobile phase: 90:10:0.5). The isolated material was carefully dried and dissolved in dry acetonitrile and placed on a ABI automated DNA synthesizer. The coupling time for the modified nucleoside was increased to 30 min. Mass spectral analysis of the purified material revealed the expected parent ion (M$^+$=4634 calculated; 4634 found).

$^{32}$labeling of oligonucleotides. Unmodified oligonucleotides for $^{32}$P labeling were synthesized using standard solid phase techniques. LSP 5'-TCTGCATTGTCCGA and LTP 5'-TCGGACAATGCAGA. Both LTP and LSP were labeled using $^{32-}$P(gamma)-ATP and T4 polynucleotide kinase by standard procedures. These sequences were designed in such a way that any shift of one strand in the duplex with respect to another would only allow formation of at most two Watson-Crick pairs, thus ensuring an "all-or-none" type of binding. $^{32}$P experiments were using 1 picomole of DNA in 50 µl hybridization solution. Counts were measured on a Beckman Model LS-1801 scintillation counter.

Fluorescently labeled oligonucleotides. Fluorescent oligonucleotides were synthesized using standard solid phase techniques incorporating a linker fluorescein phosphoramidite (Glen Research) at the 5' ends. LST 5'-Fluorescein-TCTGCATTGTCCGA and LTF 5'-fluorescing-TCGGACAATGCAGA were prepared and the modified oligonucleotides purified by HPLC (Waters) employing a C-18 reversed-phase column. A gradient of 2 to 40% of CH$_3$CN in and 0.1 M triethylammonium acetate, pH 6.5 was used as the mobile phase. Identities of peaks have been confirmed by coinjections of authentic samples and by enzymatic digestion (alkaline phosphatase, phosphodiesterase) followed by HPLC analysis of the nucleoside composition. Fluorescent experiments were performed using 10 nanomoles of DNA in 50 µl of solution.

Gold surface modification. A mixture of LT16 at 1 micromolar and SH-C16-OH at 50–500 micromolar in 50 mM triethylammonium acetate (pH 7.0) 25% EtOH was carefully applied to the gold surface. The ratio of solution concentration of both thiols was chosen to significantly dilute the DNA surface density ensuring that the neighboring DNA strands did not interfere with the binding abilities of one another. 20 µl were applied in each experiment. By carefully applying the solution with a pipette tip, the volume covers a 1.5 cm diameter circle. The sample was incubated overnight at room temperature in a humid chamber. The samples were rinsed with 1:3 EtOH:H$_2$O and then with H$_2$O.

Hybridization of Labeled Oligonucleotides. All hybridization experiments were performed in 6×SSC (Saline Sodium Citrate, NaCl is 0.9 M, sodium citrate is 0.09M in 6×) at 37° C. overnight. After hybridization, the sample was washed 3 times with 3×SSC buffer at room temperature for 10 minutes each and 1 time with 6×SSC at 40° C. for 30 minutes. Samples that were hybridized with oligomer complementary with the one attached to the surface showed more than 10 times higher activity level than samples that were reacted with a non-complementary oligomer. Gold surfaces coated with HS—(CH$_2$)$_{16}$—OH monolayer, in the absence of nucleic acid, and reacted with either LS or LT did not show significant counts above the background activity. Therefore, the formation of a mixed self-assembled monolayer resulted in covalent attachment of DNA strands to the surface without significant losses in binding activity and specificity.

Melting temperature determination. Unlabeled LSP and LTP sequences were dissolved in SSC at various Na+ concentrations, and Tm's were determined by measuring UV260 absorbance at increasing temperature on a Hewlett-Packard UV/vis with Peltier temperature control accessory.

We claim:

1. An array of nucleic acids comprising a solid support having a plurality of regions, each region comprising an electrode comprising a self-assembled monolayer comprising:
   a) blocking moieties, having a first end attached to said electrode, wherein said blocking moieties shield nucleic acids from said electrode; and
   b) at least one modified nucleic acid, comprising a nucleic acid and a linker moiety having a first and second end, wherein said first end of said linker is attached to said electrode and said second end is attached to said nucleic acid; wherein at least two different regions comprise different nucleic acids.

2. An array according to claim 1 wherein said first end of said blocking moieties is attached to said electrode via a sulfur linkage.

3. An array according to claim 1 wherein said first end of said linker is attached to said electrode via a sulfur linkage.

4. An array according to claim 1, 2 or 3 wherein each electrode comprises gold.

5. An array according to claim 1 wherein said blocking moieties have the formula:

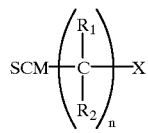

wherein

SCM is a sulfur-containing moiety, wherein said sulfur containing moiety is attached to said electrode;

$R_1$ and $R_2$ are independently selected from the group consisting of hydrogen and substituent groups;

n is an integer from 3 to 50; and

X is a terminal group.

6. An array according to claim 5 wherein $R^1$ and $R_2$ are hydrogen.

7. An array according to claim 1 wherein said blocking moieties comprise alkyl.

8. An array according to claim 5, 6 or 7 wherein n is $\geq 6$.

9. An array according to claim 1 wherein said blocking moiety is a branched molecule.

10. An array according to claim 1 wherein said linker moiety is a straight chain alkyl group.

11. A straight chain alkyl group according to claim 10 wherein said chain ranges from 1 to 20 carbon atoms.

12. An array according to claim 1 wherein at least two of said blocking moieties are different.

13. An array according to claim 1 wherein at least one of said blocking moieties is a branched molecule.

14. An array according to claim 12 or 13 wherein at least one of said blocking moieties is an alkyl group.

15. An array according to claim 1 wherein said linker moiety has the formula:

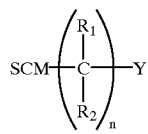

wherein

SCM is a sulfur-containing moiety, wherein said sulfur containing moiety is attached to said electrode;

$R_1$ and $R_2$ are independently selected from the group consisting of hydrogen and substituent groups;

n is an integer from 3 to 50; and

Y is the point of attachment for a nucleic acid.

16. An array according to claim 15 wherein said linker moiety is a straight chain alkyl group.

17. A straight chain alkyl group according to claim 16 wherein said chain ranges from 1 to 20 carbon atoms.

18. An array according to claim 1 wherein said modified nucleic acids have the formula:

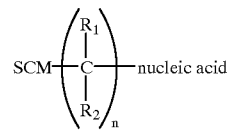

wherein

SCM is a sulfur-containing moiety, wherein said sulfur containing moiety is attached to said electrode;

$R_1$ and $R^2$ are independently selected from the group consisting of hydrogen and substituent groups; and n is an integer from 3 to 50.

19. An array according to claim 18 wherein $R_1$ and $R_2$ are hydrogen.

20. An array according to claim 15, 18 or 19 wherein n is $\geq 6$.

21. An array according to claim 1 wherein said blocking moiety comprises a phosphorus-containing moiety.

22. An array according to claim 1 wherein said nucleic acid is attached to said linker at a 2' position of a ribose.

23. An array according to claim 1 wherein said nucleic acid is attached to said linker at a 3' position of a ribose.

24. An array according to claim 1 wherein said nucleic acid is attached to said linker at a base of said nucleic acid.

25. An array according to claim 1 wherein said nucleic acid is attached to said linker at a phosphate linkage of said nucleic acid.

26. An array according to claim 1 wherein said solid support is glass.

27. An array according to claim 1 wherein said solid support is plastic.

28. A method of hybridizing a probe nucleic acid to a target nucleic acid, said method comprising adding a target nucleic acid to an array of probe nucleic acids comprising a solid support having at plurality of regions, each region comprising an electrode comprising a self-assembled mixed monolayer comprising:

a) blocking moieties, having a first end attached to said electrode, wherein said blocking moieties shield nucleic acids from said electrode; and b) at least one modified nucleic acid, comprising a probe nucleic acid and a linker moiety having a first and second end, wherein said first end of said linker is attached to said solid support and said second end is attached to said nucleic acid;

wherein at least two different regions comprise different probe nucleic acids; under conditions wherein at least one of said probe nucleic acids and said target nucleic acid will hybridize to form a hybridization complex.

29. A method according to claim 28 wherein said blocking moiety is a branched molecule.

30. A method according to claim 28 wherein at least two of said blocking moieties are different.

31. A method according to claim 28 wherein said blocking moiety is a straight chain alkyl group.

32. A method according to claim 28 wherein said linker moiety is a straight chain alkyl group.

33. An alkyl chain according to claim 30 or 31 wherein said chain ranges form 1 to 20 carbon atoms.

34. A method according to claim 28 wherein said target nucleic acid is labeled.

35. A method according to claim 34 wherein said target nucleic acid is labeled with a flourescent dye.

* * * * *